United States Patent [19]
Knoepfler

[11] Patent Number: 5,628,760
[45] Date of Patent: May 13, 1997

[54] SURGICAL HOOK KNIFE

[75] Inventor: Dennis J. Knoepfler, Amelia, Ohio

[73] Assignee: NuSurg Medical, Inc., Cincinnati, Ohio

[21] Appl. No.: 395,428

[22] Filed: Feb. 28, 1995

Related U.S. Application Data

[62] Division of Ser. No. 126,511, Sep. 24, 1993, Pat. No. 5,176,695.

[51] Int. Cl.$^6$ .................................................... A61B 17/32
[52] U.S. Cl. ............................................ 606/170; 606/167
[58] Field of Search ............................ 30/353, 355, 241; 606/166, 167, 170

[56] References Cited

U.S. PATENT DOCUMENTS

| | | | |
|---|---|---|---|
| 385,353 | 7/1888 | Hilton | 30/241 |
| 1,466,753 | 9/1923 | Raubert | 30/353 |
| 1,537,308 | 5/1925 | Jenner | 30/353 |
| 2,847,758 | 8/1958 | Kozan | 30/353 |
| 3,610,246 | 10/1971 | Salmon . | |
| 3,716,056 | 2/1973 | Brodsky et al. . | |
| 4,766,896 | 8/1988 | Pao . | |
| 4,963,147 | 10/1990 | Agee et al. . | |
| 5,122,152 | 6/1992 | Mull | 606/170 |
| 5,174,300 | 12/1992 | Bales et al. . | |
| 5,176,695 | 1/1993 | Dulebohn . | |

OTHER PUBLICATIONS

Brochure, Valleylab®, "Introducing...Polaris™, Graspers, Dissectors, and Forceps", ©1992, Valleylab, Inc., Oct. 1992.
Brochure, "NuSURG® Laparoscopic Hook Knife", ©NuSURG Medical, Inc., 1992.
Brochure, Arista, "Instruments", 1992 Edition.

*Primary Examiner*—Guy V. Tucker
*Assistant Examiner*—William W. Lewis
*Attorney, Agent, or Firm*—Wood, Herron & Evans, P.L.L.

[57] ABSTRACT

A laparoscopic hook knife for use in surgical procedures includes an elongate shaft having a pistol grip handle at its proximal end and a blade support with a hook-shaped member at the distal end. The hook-shaped member has a blunt distal tip which is formed in the shape of a spade contained in a plane generally perpendicular to the plane containing the attached blade. An outlet is provided at the proximal end of the instrument for attaching a source of unipolar electric current for the purposes of creating hemostasis along the cutting path in the tissue. The shaft and blade support, except for the spade tip and at least one contact point between the blade and the blade support, are coated with an electrically insulating material to prevent any undesirable conduction of electricity. A second embodiment includes a blade member having an outer, straight cutting edge and an inner, curved cutting edge. The blade member may be moved between first and second positions in which the straight cutting edge is exposed in the first position and the curved cutting edge is exposed in the second position.

1 Claim, 2 Drawing Sheets

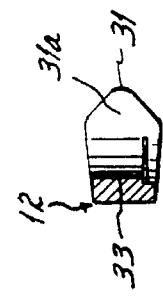
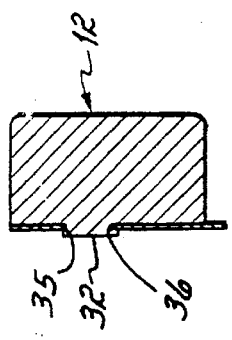
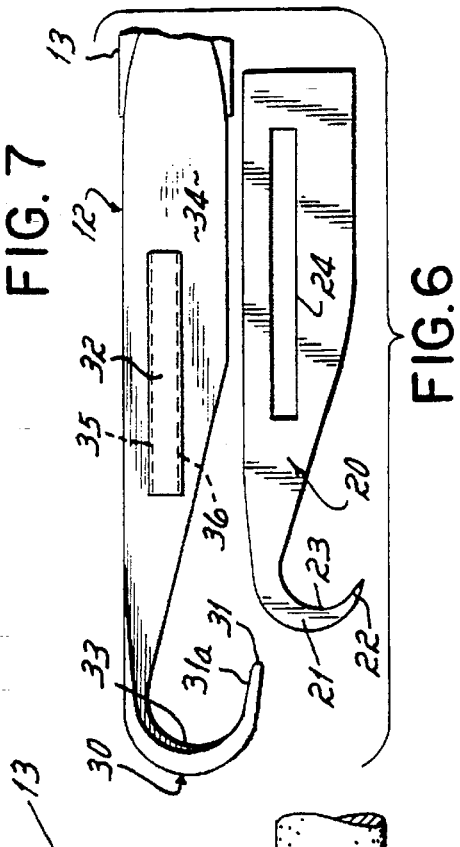
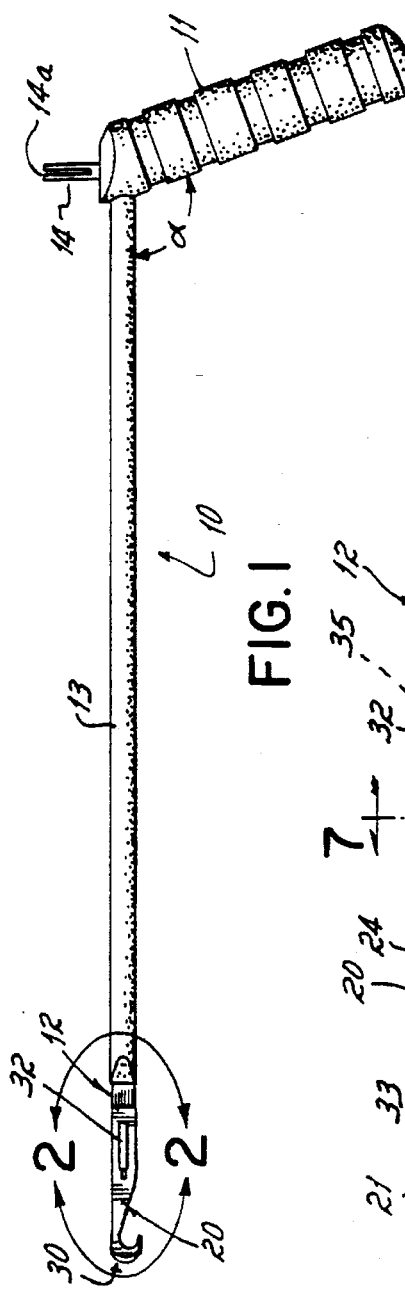
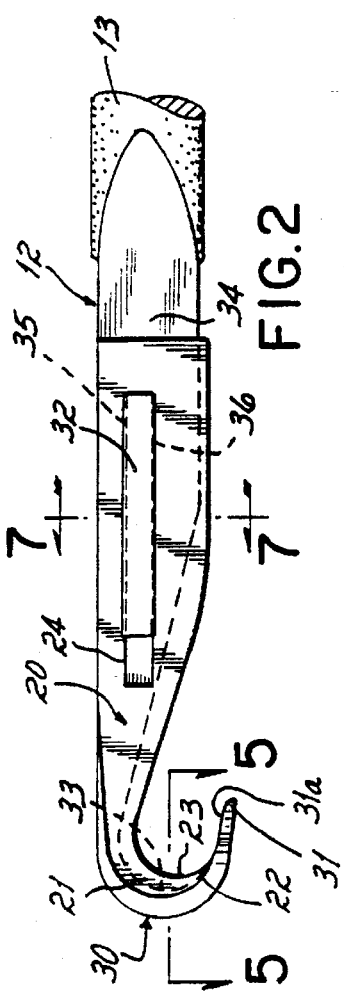
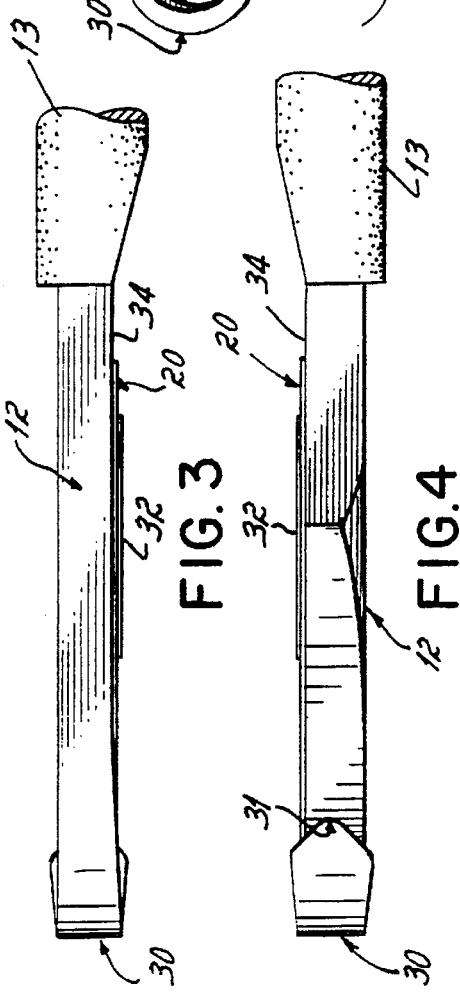

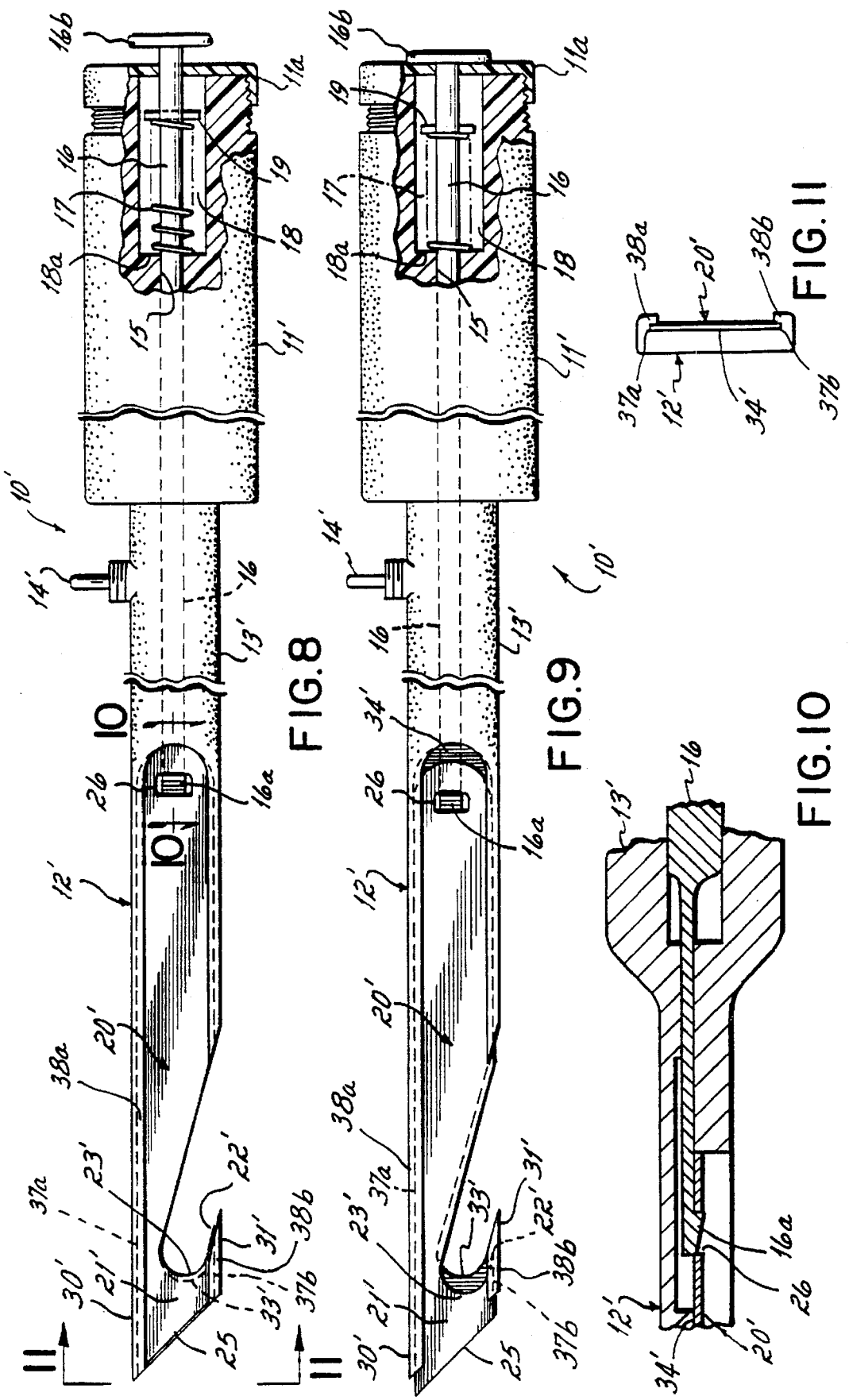

SURGICAL HOOK KNIFE

This application is a divisional of application Ser. No. 08/126,511, filed Sep. 24, 1993, now U.S. Pat. No. 5,176,695.

BACKGROUND OF THE INVENTION

The present invention generally relates to surgical cutting instruments and more particularly to a laparoscopic instrument having a hook-shaped blade structure.

A wide variety of bladed instruments have been developed for use in surgical procedures. Many specialized shapes have been used for the blades of such instruments to allow the surgeon to easily make different types of incisions and cuts in tissue. In the past, instruments with curved blades have been utilized in operations to make certain specialized cuts easily and with reduced trauma to surrounding tissue.

One surgical instrument employing a curved blade is shown and described in U.S. Pat. No. 3,610,246 to Salmon. This patent discloses a knife blade having a curved cutting edge and including two protuberances along either side of the rear of the blade. The protuberances are employed so that the two cut edges of a membrane or blood vessel ride along the top of the protuberances to cause the walls of the membrane or vessel to be spread apart as the surgeon makes the cut.

Certain disadvantages are associated with typical curved blade instruments such as the tendency for such blades to stray from the intended cutting path and thereby damage surrounding tissue.

Accordingly, it has been one object of the present invention to provide a hook-shaped knife having a specialized tip design for allowing dissection in a select tissue plane without injuring deeper tissue structure.

It has been another object of the invention to provide a knife having an electrical coagulation outlet electrically connected to the blade for enabling hemostasis and further having an electrically insulative coating on other parts of the instrument to prevent damage to surrounding tissue.

It has been still another object of the invention to speed certain surgical operations through the use of a single cutting instrument having a dual cutting edge blade which allows two distinct cutting operations to be performed on tissue.

SUMMARY OF THE INVENTION

To these ends, a first embodiment of the present invention provides an instrument having an elongate shaft with a pistol grip handle attached at its proximal end and a blade support on its distal end. The blade support corresponds in shape to a hook-shaped blade member which is removably attachable to the blade support. The blade support includes a distal hook member having a blunt tip. The blunt tip is preferably shaped in the form of a spade which lies in a plane generally perpendicular to the plane of an attached blade member.

As previously mentioned, the blade member has a hook-shaped distal end that generally follows the shape of the distal hook member of the blade support. A cutting edge is formed along the inside curved edge of the hook-shaped distal end of the blade member. When properly attached to the blade support, the curved cutting edge of the blade member will be positioned proximally of the inside edge of the distal hook member. Also, the outer tip of the blade member will lie inside or distally of the end of the spade-shaped tip.

The instrument includes an outlet for connecting a supply of unipolar electric current to the instrument to be supplied to the blade member for the purposes of causing hemostasis to occur along the cutting path. The outlet preferably is formed as an electrically conductive pin extending upwardly from the handle. The pin is connected to the shaft which is also preferably formed from an electrically conductive material, such as stainless steel, so as to conduct current to the blade member. The shaft and blade support of the instrument are preferably coated with an electrically insulating material to prevent unwanted conduction of electric current to the patient, physician or surrounding environment.

A second embodiment of the invention provides an instrument including an elongated shaft having a hook-shaped distal end similar to that of the first embodiment but including a blade support having opposed blade support surfaces for supporting opposite sides of the blade. The blade structure of the second embodiment also differs from that of the first embodiment. In this regard, the blade of the second embodiment includes both an inner, curved cutting edge and a straight, distal cutting edge. The blade support includes a distal slot for receiving the distal end of the blade having the straight cutting edge. The shaft is hollow and a handle is attached at its proximal end.

The elongated shaft houses a spring-loaded push rod having an actuating knob at its proximal end. The actuating knob preferably extends outwardly from the handle so that it may be operated, for example, by the surgeon's thumb. The push rod extends within the hollow shaft to a point proximate the hook-shaped distal end of the shaft. At its distal end, the push rod includes means for attaching the blade member thereto. This may, for example, be a hook shaped structure on the distal end of the push rod which grasps the blade through an aperture therein.

The handle of the instrument preferably holds a compression spring which is connected to the push rod so that the push rod may be extended against the force of the spring when the surgeon depresses the actuating knob. Extension of the push rod in this manner causes the straight, distal cutting edge of the blade to extend through a slot at the distal end of the elongated instrument shaft. This allows the surgeon to make an initial cut in the patient's tissue which may, for example, be a hollow tubular organ or viscus. After the initial cut is made, the surgeon releases the actuating knob allowing the force of the spring to retract the blade into a position exposing the curved, inner edge of the blade. Thus positioned, the blade may be used to make a lengthwise cut in the tissue by inserting the hook-shaped distal end of the instrument into the initial cut and pulling the curved, inner cutting edge along the tissue.

Various other aspects and advantages and objects of the invention will become readily apparent to those of ordinary skill from the following detailed description taken in conjunction with the accompanying drawings.

BRIEF DESCRIPTION OF THE DRAWINGS

FIG. 1 is an elevated side view of a first embodiment of the surgical cutting instrument of the invention;

FIG. 2 is an enlarged view of encircled portion 2 of FIG. 1 showing the distal end of the instrument;

FIG. 3 is a top view of the distal end of the cutting instrument shown in FIG. 2;

FIG. 4 is a bottom view of the distal end of the cutting instrument shown in FIG. 3;

FIG. 5 is a cross sectional view of the distal end of the cutting instrument taken along line 5—5 of FIG. 2;

FIG. 6 is a side view similar to FIG. 2 but showing the blade removed from the instrument;

FIG. 7 is a cross sectional view of the cutting instrument taken along line 6—6 of FIG. 2;

FIG. 8 is an elevated side view of a second embodiment of a cutting instrument of the invention having a dual position, double edged blade member shown in a first cutting position and partially fragmented to show inner details of the instrument;

FIG. 9 is a side view of the instrument of FIG. 8 but showing the blade member in a second cutting position;

FIG. 10 is a cross sectional view of the cutting instrument taken along line 10—10 of FIG. 8; and, FIG. 11 is an end view of the cutting instrument taken along line 11—11 of FIG. 8.

DETAILED DESCRIPTION OF THE PREFERRED EMBODIMENTS

FIGS. 1-7 illustrate a first embodiment of the invention. Referring first to FIG. 1, a first embodiment of the hook knife 10 of the present invention is shown to generally include an elongated shaft 13 with a handle member 11 disposed at a proximal end and a blade support 12 disposed at a distal end thereof. The handle member 11 is attached to the shaft 13 at an obtuse angle α with respect to the shaft 13. Although the angle α may be anywhere in the range of 90° to 180°, the device has been found easiest to manipulate when the handle is attached at a preferred angle α of about 120°.

An electrical outlet pin 14 extends upwardly from a top surface of the handle 11 and includes a slot 14a which allows for the attachment of a wire for supplying electric current to the outlet pin 14. The outlet pin 14 is electrically connected to the blade support 12 preferably via the shaft 13. The shaft 13 and blade support 12 are both formed from an electrically conductive material, such as a suitable surgical grade stainless steel, to allow conduction of electricity from the outlet pin 14 to the shaft 13 and the blade support 12.

The shaft 13 and the blade support 12 are preferably coated with an electrical insulating material to prevent the conduction of electric current to the outside surfaces of these areas of the instrument and in turn to the patient, surgeon or surroundings. A preferred coating material which will also minimize the chances of the instrument sticking during the surgical procedure is Teflon®. The handle 11 is preferably formed from an electrically nonconducting material such as rubber or plastic.

As shown best in FIGS. 2 and 6, the hook knife utilizes a disposable blade 20 having a hook-shaped distal end 21 which preferably converges into a sharpened tip 22. The blade 20 is preferably formed from medical grade stainless steel and has a curved, inner cutting edge 23. The blade 20 further includes a central, elongated slot 24 which is used to attach the blade 20 to the blade support 12.

As further shown in FIG. 2, the blade support 12 includes a "C" shaped distal hook member 30 having an outer tip 31 that is disposed beyond the tip 22 of the attached blade 20. The outer tip 31 of the "C" shaped hook 30 is formed in the shape of a spade in a plane transverse to the plane of the attached blade 20 (see FIGS. 2 and 4). The spade-shaped tip 31 is contained in a plane transverse to the plane of the attached blade 20 to allow the operator to dissect tissue in a select plane without injuring surrounding tissue. The blade support 12 further includes an elongated raised portion 32 extending from a flat, blade supporting surface 34 and having lengthwise grooves 35, 36 along the sides thereof for retaining the blade 20 in place.

As illustrated in FIGS. 2-4, the blade 20, which is typically thin and flexible, is supported on one side by the flat surface 34 of the blade support 12. The blade 20 is firmly attached to the blade support 12 by aligning the slot 24 in the blade 20 over the raised portion 32 on the blade support 12 and press fitting the blade 20 into place. When the blade 20 is properly attached to the blade support 12, the edges of the slot 24 are received by the grooves 35, 36 on either side of the raised portion 32 (see FIG. 7). In this attached position, the curved, inner cutting edge 23 of the blade 20 extends proximally a short distance from the curved inside edge 33 of the hook member 30.

As previously stated, the shaft 13 and the blade support 12 are coated with an insulating material such as Teflon®, however, the spade-shaped tip 31 of the hook member 30 may be left uncoated to cause hemostasis as the spade-shaped tip 31 is pulled through the tissue during surgery. The surfaces of the grooves 35, 36 which are in contact with the blade 20 are also left uncoated by insulating material to allow electric current to flow between the blade support 12 and the blade 20 and in turn to the tissue so as to cause hemostasis to occur as the tissue is cut by the blade 20.

A second embodiment of the present invention will now be described with reference to FIGS. 8-11, in which like reference numerals have a prime mark and represent like elements of the first and second embodiments of the invention. As shown in FIGS. 8 and 9, the hook knife 10' includes a handle member 11' and a blade support 12' at the proximal and distal ends, respectively, of an elongated shaft 13'. Although, like the embodiment shown in FIGS. 1-7, the handle member 11' may be disposed at an angle transverse to the elongated shaft 13', it has been shown in FIGS. 8 and 9 to be co-linear with the elongated shaft 13'. The hook knife 10' is further provided with an electrical outlet pin 14' which, like the first embodiment, includes a slot (not shown) which allows a wire to be attached to the outlet pin 14' to supply electric current to the hook knife 10' for purposes of hemostasis.

The hook knife 10' further includes an elongated central bore 15 which extends along the length of the handle member 11' and the elongated shaft 13'. The bore 15 receives a spring loaded push rod 16 having a hook-shaped catch 16a at its distal end and an actuating knob 16b at its proximal end. If the handle member 11' is disposed at an angle to the shaft 13', the actuating knob may be conveniently disposed at the top of the handle for easy access by the thumb of the user. The handle member 11' houses a spring 17 within a cavity 18 of the handle 11'. The spring 17 allows the push rod 16 to be moved from a first position to a second position, and when the actuating knob 16b is released, to automatically revert back to the first position. The compression spring 17 is captured between an end wall 18a of the cavity 18 and a stop 19 which is rigidly secured to the plunger 16. To allow the plunger 16 and the spring 17 to be readily assembled and disassembled, the handle member 11' includes a cap 11a which is threadedly secured to the proximal end of the handle 11'.

The blade 20' includes a hook-shaped portion 21' having an inner curved cutting edge 23' ending at an outer tip 22'. The blade 20' further includes a straight cutting edge 25 on its outer distal end. At its opposite, proximal end, the blade 20' is attached to the push rod 16 by way of the hook-shaped clasp portion 16a of the push rod 16, which is received by an aperture 26 in the blade member 20' (see FIG. 10). Of course, any one of a number of fastening means may be substituted for the clasp portion 16a. Some examples would include threaded fasteners, pins, or a spring detent mechanism.

With reference to FIGS. 8 and 9, the blade support 12' includes a distal, generally hook-shaped portion 30' which includes an outer guide tip 31'. Although not specifically illustrated in FIGS. 8–11, the outer guide tip 31' may, like the hook knife of the first embodiment, be formed in the shape of a spade when viewed in a plane generally perpendicular to the attached blade 20'. As best seen in FIG. 11, the hook-shaped distal portion 30' has upper and lower slots or openings, 37a, 37b formed by flanges 38a, 38b allowing access by the blade 20' to the inside of the distal portion 30', i.e., the space between flanges 38a, 38b and blade support surface 34'.

As specifically shown in FIGS. 9 and 10, the blade 20' is slidably received between the flanges 38a, 38b and inner blade supporting surface 34' of the hook-shaped distal portion 30'. Thus, as the plunger 16 is moved back and forth, the blade 20' may slide between a first position in which the curved, inner cutting edge 23' of the blade 20' is exposed for cutting tissue and a second position in which the straight, outer cutting edge 25 is exposed for cutting tissue. It will be appreciated that the compression spring 17 is sufficiently stiff to prevent the push rod 16 and blade member 20' from moving in a distal direction, i.e., from the first position to the second position, when the physician is pulling the hook knife 10' along tissue using the curved inner cutting edge 23'.

Operation

In describing the operation of an instrument constructed according to the first embodiment of the invention, reference is first made to FIG. 6 in which a disposable blade 20 is shown unassembled from the blade support 12 of the instrument 10. As previously mentioned, a sterile blade 20 is snapped onto the raised portion 32 of the blade support 12 by inserting the raised portion 32 into the slot 24 of the blade 20. The operator then slides the blade 20 toward the distal end of the blade support 12 such that the blade 20 is positioned as shown in FIG. 2. With regard to the second embodiment and particularly to FIGS. 8–11, the blade 20' is attached to the instrument 10' by carefully sliding the blade 20' into the slots 37a, 37b between the flanges 38a, 38b and the blade support surface 34 until the clasp portion 16a of the push rod 16 engages the aperture 26 in the blade 20'. If desired during a particular operation, a unipolar source of electric current is then connected to the outlet 14 to cauterize the tissue as it is cut.

A hook knife made in accordance with the preferred embodiments of the present invention is especially useful in making cuts along the length of, for example, the common bile duct. In preparation for using the hook knife of either the first or second embodiment of the invention in such operations, the surgeon makes an initial incision in the common bile duct. When the hook knife 10 of the first embodiment is used, this initial cut is made with a conventional scalpel. When the hook knife 10' of the second embodiment is used, the blade 20' is actuated to the second position by the depressing the knob 16b and this cut is made with the straight, outer cutting edge 25 of the blade member 20'. In either case, this initial incision must be large enough to enable the surgeon to insert the hook-shaped distal end of the hook knife 10 or 10' into the incision.

The actual lengthwise cutting action of the two embodiments of the present invention is the same and therefore reference will now only be made to the hook knife 10 of the first embodiment. Using the spade-shaped tip 31 as a locating guide, the surgeon pulls the hook member 30 along the desired path allowing the inside surface 31a of the spade-shaped outer tip 31 to ride along the inside wall of the common bile duct as it is cut. This causes tissue to ride up over the spade-shaped tip 31 and into the blade 20 where it is divided by the cutting edge 23. If a source of electric current is connected to the outlet 14, then the cut edges of the tissue are simultaneously cauterized by the blade 20.

Accordingly, the present invention provides a laparoscopic knife which allows the operator to easily cut tissue along a path in a select tissue plane without damaging surrounding tissue and further creates simultaneous hemostasis along the cutting path.

Moreover, the spade-shaped tip of the present invention allows the surgeon to make long, straight cuts in vessels, viscera and other organs by using an easy, accurate pulling motion instead of a more difficult and less accurate slicing motion.

In addition, an instrument constructed according to the second embodiment of the invention allows a surgeon to use a single cutting instrument to safely and efficiently make cuts in tissue as described above.

Although preferred embodiments of the present invention have been shown and described in detail, certain modifications will be readily apparent to those of ordinary skill in the art without departing from the spirit and scope of the invention and applicant intends only to be bound by the claims appended hereto.

I claim:

1. A blade member for use with a surgical cutting instrument, said blade member including two side edges extending between proximal and distal ends of said blade member, a curved cutting edge extending inwardly from one of said side edges intermediate said proximal and distal ends, said curved cutting edge generally facing in a proximal direction and an outer, generally straight cutting edge disposed on said distal end and facing in a direction generally opposite to said curved cutting edge.

* * * * *